US009161127B2

(12) United States Patent
Hung et al.

(10) Patent No.: US 9,161,127 B2
(45) Date of Patent: Oct. 13, 2015

(54) SIGNAL PROCESSING APPARATUS

(75) Inventors: Chia-Yu Hung, Hsinchu County (TW); Tsung-Li Yeh, Hsinchu (TW); Yi-Chang Tu, New Taipei (TW)

(73) Assignee: Realtek Semiconductor Corp., Science Park, HsinChu (TW)

( * ) Notice: Subject to any disclaimer, the term of this patent is extended or adjusted under 35 U.S.C. 154(b) by 611 days.

(21) Appl. No.: 13/563,752

(22) Filed: Aug. 1, 2012

(65) Prior Publication Data

US 2013/0034236 A1 Feb. 7, 2013

(30) Foreign Application Priority Data

Aug. 2, 2011 (TW) ............................ 100127390 A

(51) Int. Cl.

*A61F 11/06* (2006.01)
*G10K 11/16* (2006.01)
*H03B 29/00* (2006.01)
*H04R 3/02* (2006.01)
*H04R 3/00* (2006.01)

(52) U.S. Cl.

CPC ... *H04R 3/02* (2013.01); *H04R 3/00* (2013.01)

(58) Field of Classification Search

CPC .......... H04R 3/02; H04R 3/00; H04R 1/1083; H04R 1/1041; H04R 2460/01

USPC ............. 381/71.1, 94.1, 74, 122, 123; 700/94

See application file for complete search history.

(56) References Cited

U.S. PATENT DOCUMENTS 4,494,074 A 1/1985 Bose
5,138,664 A 8/1992 Kimura
7,592,941 B2 9/2009 Ohkuri
2008/0112570 A1 * 5/2008 Asada et al. ................ 381/71.6
2009/0046867 A1 2/2009 Clemow
2009/0295615 A1 12/2009 Steiner

FOREIGN PATENT DOCUMENTS

CN 1684189 A 10/2005
CN 101001481 A 7/2007
TW I279775 4/2007

* cited by examiner

*Primary Examiner* — Paul S Kim
(74) *Attorney, Agent, or Firm* — Winston Hsu; Scott Margo

(57) ABSTRACT

A signal processing apparatus for generating a noise cancellation signal in accordance with a noise signal includes an inverting circuit and a selecting circuit. The inverting circuit is employed for inverting a first signal to generate an inverted first signal. The selecting circuit is coupled to the inverting circuit, and employed for selecting one of the first signal and the inverted first signal as an output signal.

12 Claims, 10 Drawing Sheets

SIGNAL PROCESSING APPARATUS

BACKGROUND OF THE INVENTION

1. Field of the Invention

The present invention relates generally to signal processing, and more particularly, to a signal processing apparatus for performing active noise control.

2. Description of the Prior Art

The concept of active noise control method is to generate an 'anti-noise', which has an amplitude that is substantially identical to a noise source in the environment, but is substantially opposite in phase to the noise source (in practice, the anti-noise may only be similar to the noise source in the low frequency part). By superposition of the sound wave, the noise source and the anti-noise destructively interfere with each other, thereby eliminating the noise. This technology is generally used in a variety of loudspeaker devices, such as headphones. When a user is listening to audio materials via a loudspeaker, the loudspeaker device simultaneously produces the anti-noise by mixing an audio signal corresponding to audio materials with a noise cancellation signal corresponding to the anti-noise. As a result, the user will not be aware of the noise, and the listening experience will be improved. Conventionally, active noise control technology can be implemented by the circuit shown in FIG. 1.

A conventional noise cancellation apparatus illustrated in FIG. 1 includes an acoustic-to-electric transducer 11 (e.g. a microphone), an analog-to-digital converter 12, a filtering circuit 13 and a digital-to-analog converter 14. The acoustic-to-electric transducer 11 is employed for recording noises in the environment, and uses piezoelectricity generation to generate an electrical analog noise signal. The analog-to-digital converter 12 converts the analog noise signal into a digitalized noise signal. The digitalized noise signal will be passed to the filtering circuit 13, which filters the digitalized noise signal based on a transfer function depending on how much of the noise is actually received by the user, to generate a noise cancellation signal which is used to destructively interfere with the noise. An output of the filtering circuit 13 may be further converted to an analog signal by the digital-to-analog converter 14. The analog signal will be processed by an electric-to-acoustic transducer 15 to generate an analog noise cancellation signal. The analog noise cancellation signal will be mixed with an audio signal intended for playback by a mixer 16. After mixing, the user will be unaware of noises in the environment while listening to the audio.

This circuit architecture has certain problems, however. For example, under the consideration of signal gain, the analog signal may be processed by more than one amplifying stage, which may include inverse amplifying stages, before being transmitted to the mixer 16 or the electric-to-acoustic transducer 15. This may cause the analog noise cancellation signal to be inverted twice, which will result in the signal constructively interfering with the noise. Since the purpose of the analog noise cancellation signal is to destructively interfere with the noise, the conventional noise cancellation apparatus is unable to resolve this problem.

SUMMARY OF THE INVENTION

It is one objective of the present invention to provide a signal processing apparatus for noise cancellation based on an active noise control method. The signal processing apparatus can output a noise cancellation signal of different polarities to overcome the problems encountered in the conventional art. The signal processing apparatus utilizes an inverting circuit and a selecting circuit to determine what polarity is outputted. Depending on the design of a back-stage circuit coupled to the signal processing apparatus, the signal processing apparatus can be configured to select either an inverted noise cancellation signal (which is substantially the same in phase as the noise) or a non-inverted noise cancellation signal (which is substantially opposite in phase to the noise) to be output. Even if the back-stage circuit inversely amplifies the noise cancellation signal, the inventive signal processing apparatus can provide the noise cancellation signal in a proper phase such that the signal processing apparatus can still destructively interfere with the noise, which successfully provides the noise cancellation function.

According to one embodiment of the present invention, a signal processing apparatus is provided. The signal processing apparatus receives a noise signal to accordingly generate a noise cancellation signal. The signal processing apparatus comprises an inverting circuit and a selecting circuit. The inverting circuit is employed for inverting a first signal to generate an inverted first signal. The selecting circuit is coupled to the inverting circuit, and employed for selecting one of the first signal and the inverted first signal as an output signal.

Preferably, the signal processing apparatus further comprises a filtering circuit. The filtering circuit is coupled to the selecting circuit, and employed for filtering the output signal to generate the noise cancellation signal, wherein the first signal is the noise signal.

Preferably, the signal processing apparatus further comprises a filtering circuit. The filtering circuit is coupled to the inverting circuit, and employed for filtering the noise signal to generate the first signal.

According to another exemplary embodiment of the present invention, a signal processing apparatus is provided. The signal processing apparatus is employed for receiving a noise signal and accordingly generating a noise cancellation signal. The signal processing apparatus comprises an inverting circuit, a filtering circuit and a selecting circuit. The inverting circuit is employed for inverting the noise signal to generate an inverted noise signal. The filtering circuit is coupled to the inverting circuit for filtering the noise signal and the inverted noise signal to generate a filtered noise signal and a filtered inverted noise signal. The selecting circuit is coupled to the filtering circuit, and employed for selecting one of the filtered noise signal and the filtered inverted noise signal as the noise cancellation signal.

These and other objectives of the present invention will no doubt become obvious to those of ordinary skill in the art after reading the following detailed description of the preferred embodiment that is illustrated in the various figures and drawings.

DETAILED DESCRIPTION

The inventive signal processing apparatus comprises an inverting circuit, a filtering circuit and a selecting circuit. The signal processing apparatus is employed for receiving a noise signal to generate a noise cancellation signal. The purpose of the filtering circuit is to generate a noise cancellation signal which is similar to the noise in the environment (but they are in anti-phase). The inverting circuit is employed for generating signals having different polarities. With the selecting circuit, it can be determined whether or not to generate the inverted noise cancellation signal or the non-inverted noise cancellation signal. The selecting circuit can change the polarity of the output signal based on different circuit designs. According to various embodiments of the present invention, the inverting circuit, the filtering circuit and the selecting circuit can be arranged in various ways, which are illustrated as follows.

Figure 1:
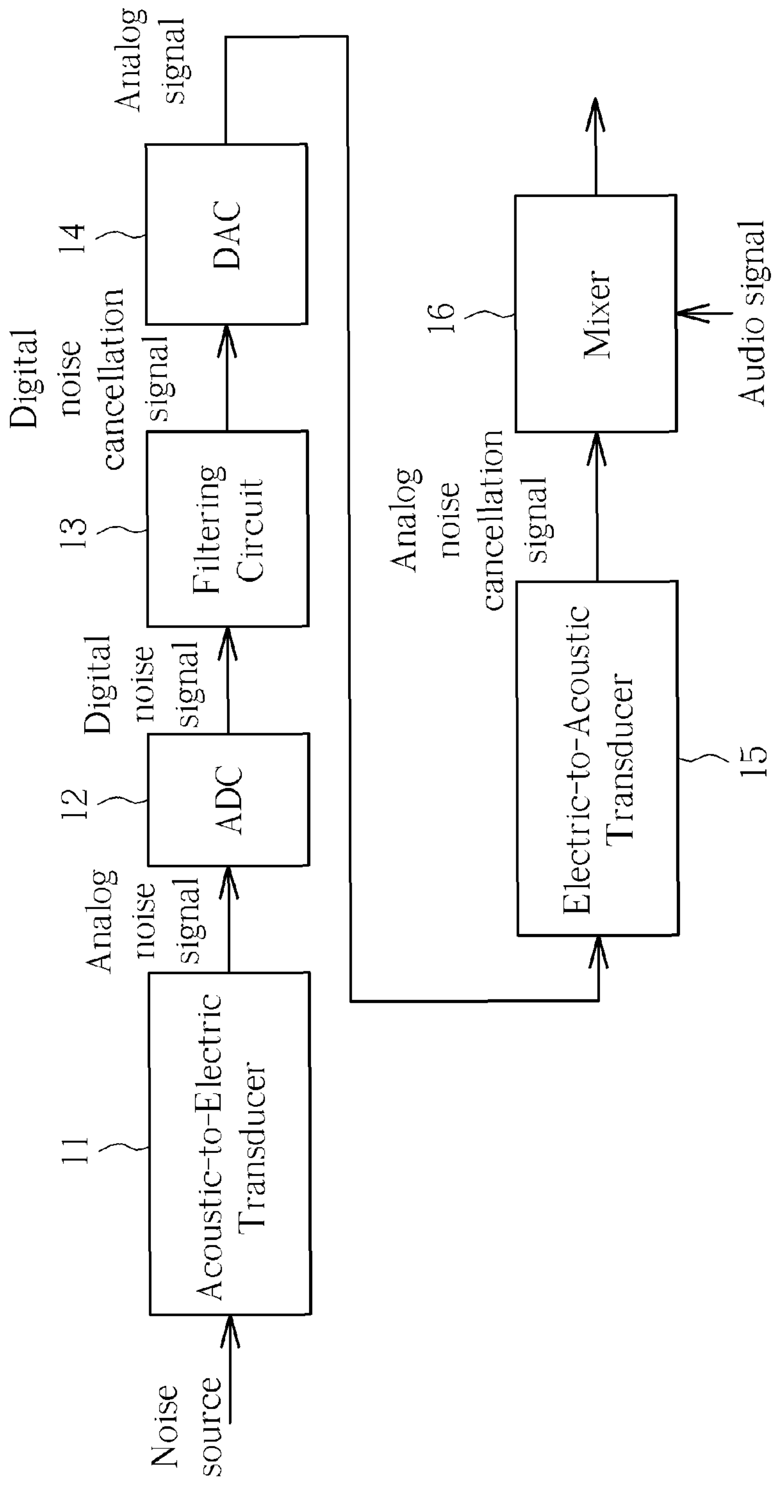
FIG. 1 PRIOR ART
FIG. 1 illustrates a conventional noise cancellation apparatus.
Figure 2:
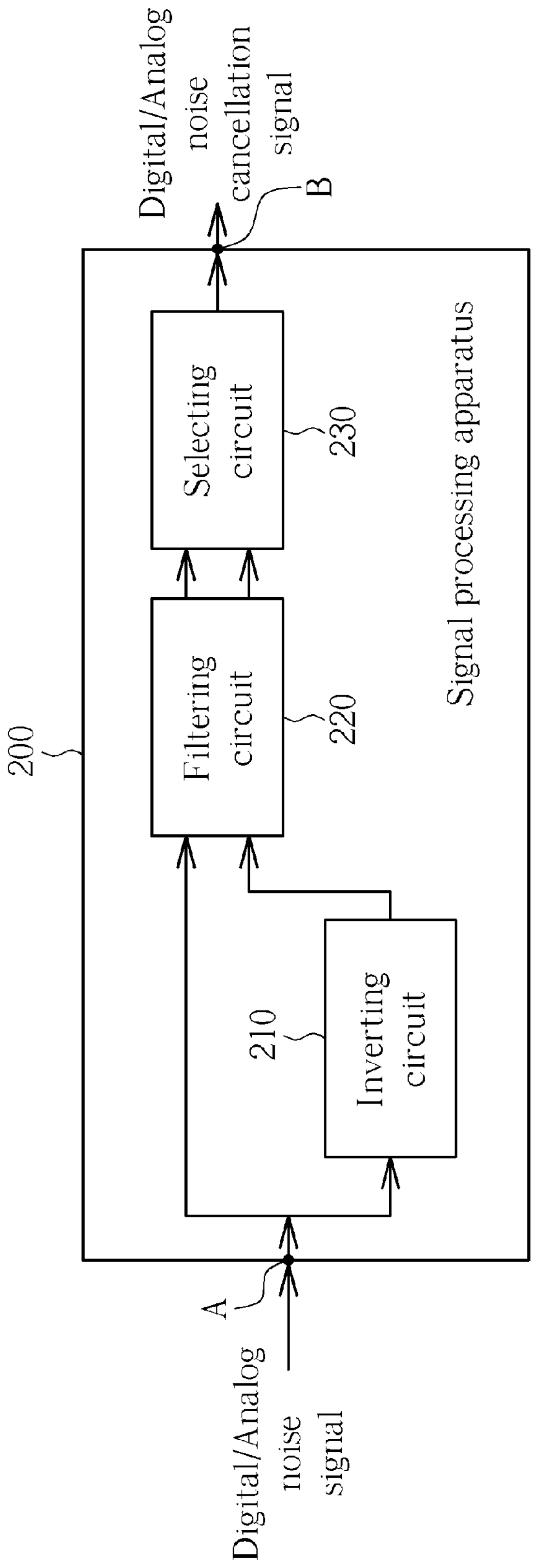
FIG. 2 illustrates a block diagram of a signal processing apparatus according to a first exemplary embodiment of the present invention.

FIG. 2 illustrates a first exemplary embodiment of the present invention. In this embodiment, a signal processing apparatus 200 receives a noise signal to generate a noise cancellation signal, wherein the noise signal may be derived by an acoustic-to-electric transducer (not shown) generating an analog noise signal according to the noise source in the environment. Further, the analog signal may be processed by an analog-to-digital converted (not shown) to become a digital noise signal. The noise cancellation signal (which could be a digital signal or an analog signal) is provided to a back-stage circuit (e.g. power amplifier, electric-to-acoustic transducer, and/or mixer) and a loudspeaker device (e.g. a loudspeaker or a headphone) for playback, thereby restraining the noise. The inverting circuit 210 is employed for receiving the noise signal, and inverting the noise signal to generate an inverted noise signal. The filtering circuit 220 is coupled to the inverting circuit 210, and employed for receiving the noise signal and the inverted noise signal. The filtering circuit 220 filters the noise signal and the inverted noise signal to generate a filtered noise signal and a filtered inverted noise signal. The selecting circuit 230 is coupled to the filtering circuit 220, and employed for selecting one of the filtered noise signal and the filtered inverted noise signal as an output signal, wherein the output signal is the noise cancellation signal provided by the signal processing apparatus 200. Briefly, in this embodiment, the inverting circuit 210 firstly generates an inverted signal according to the noise signal. The filtering circuit 220 filters both the inverted and the non-inverted noise signal. Finally, the selecting circuit 230 selects one of the two outputs of the filtering circuit 220 as the noise cancellation signal. When the back-stage circuit substantially inversely amplifies the output signal from the signal processing apparatus 200, the selecting circuit 230 will select to output the inverted noise cancellation signal; otherwise, the non-inverted noise cancellation signal will be outputted.

Figure 3:
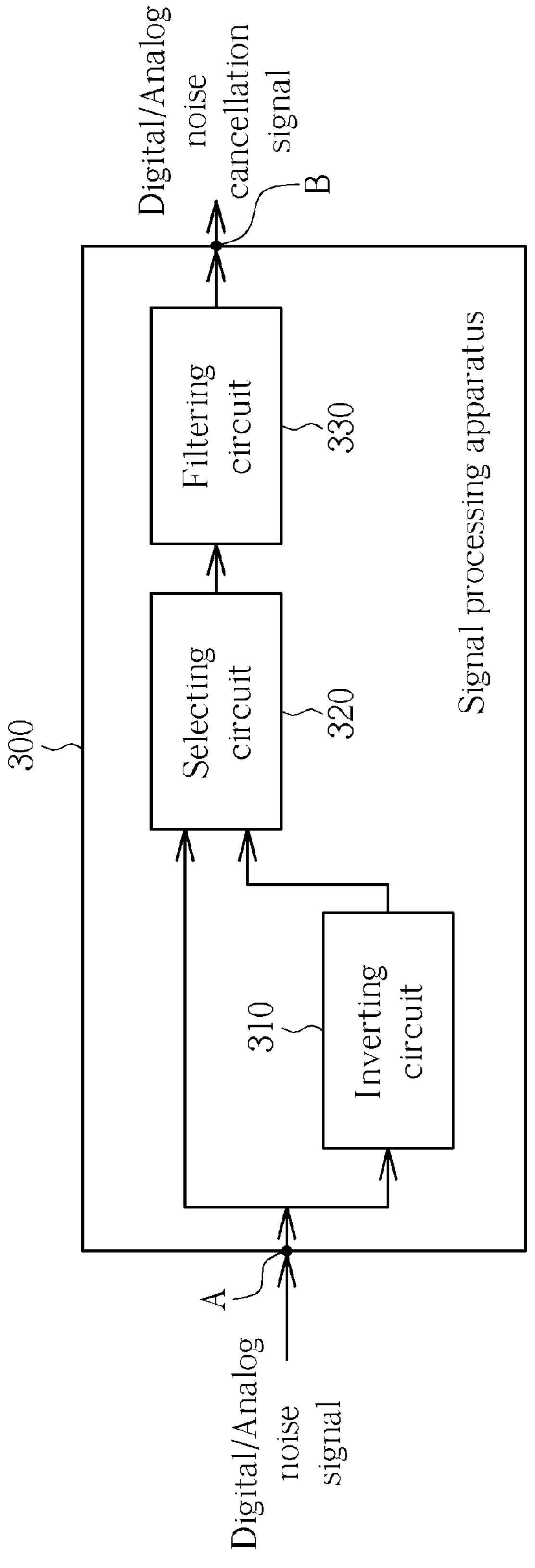
FIG. 3 illustrates a block diagram of a signal processing apparatus according to a second exemplary embodiment of the present invention.

FIG. 3 illustrates a modified embodiment of the signal processing apparatus according to a second exemplary embodiment of the present invention. As shown, the inverting circuit 310 is employed for receiving the noise signal, and accordingly inverting the noise signal to generate an inverted noise signal. The selecting circuit 320 is coupled to the inverting circuit 310, and employed for selecting one of the noise signal and the inverted noise signal as an output signal. The filtering circuit 330 is coupled to the selecting circuit 320, and employed for receiving the output signal and filtering the output signal to generate the noise cancellation signal. Briefly, in this embodiment, the selection of the signals is prior to the filtering of the signals. Hence, the filtering circuit 330 merely needs to perform filtering operation on one signal, which can reduce the complexity of the circuitry of the filtering circuit 330.

Figure 4:
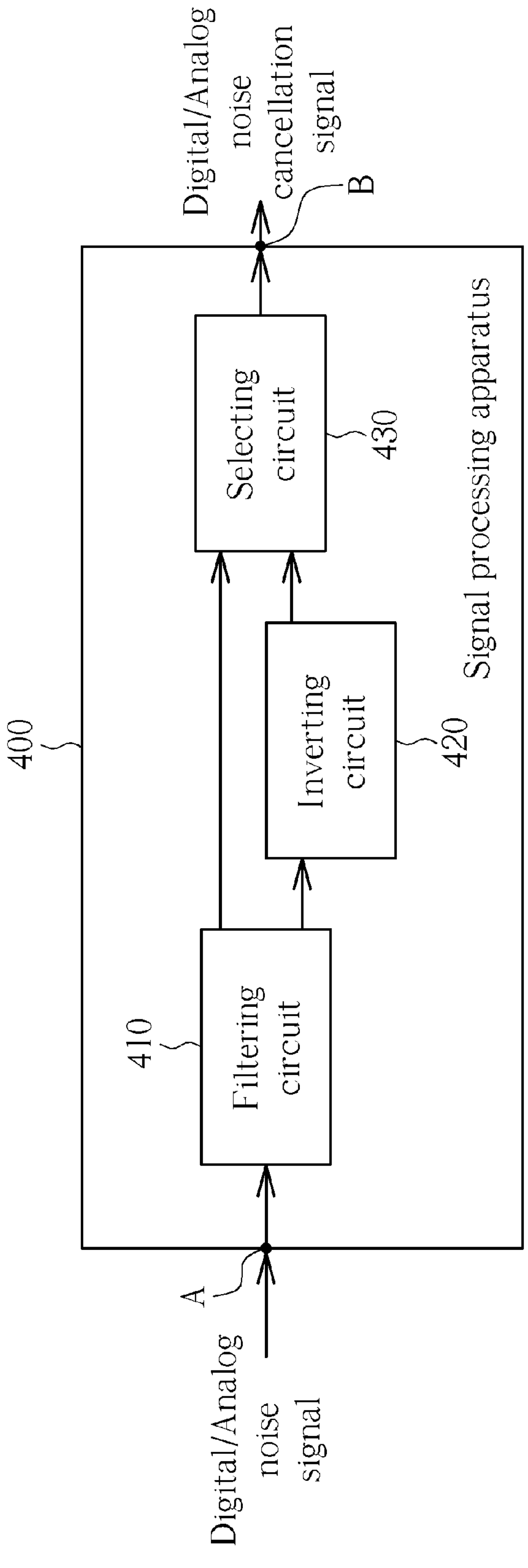
FIG. 4 illustrates a block diagram of a signal processing apparatus according to a third exemplary embodiment of the present invention.

FIG. 4 illustrates another modified embodiment of the signal processing apparatus according to a third exemplary embodiment of the present invention. As shown, the filtering circuit 410 is employed for receiving the noise signal, and for filtering the noise signal to generate a filtered noise signal. The inverting circuit 420 is coupled to the filtering circuit 410, and employed for receiving the filtered noise signal and accordingly inverting the filtered noise signal to generate an inverted filtered noise signal. The selecting circuit 430 is coupled to the inverting circuit 420 and the filtering circuit 410, and employed for receiving the inverted filtered noise signal and the filtered noise signal, and accordingly selecting one of these signals as the noise cancellation signal.

Although only the inverting circuit, the filtering circuit and selecting circuit are mentioned in the above description regarding components of the signal processing apparatus, in other embodiments of the present invention, the signal processing apparatus may include additional components, which may be coupled between any two of the inverting circuit, the filtering circuit and the selecting circuit. Alternatively, these additional components may be coupled between the input terminal (i.e. terminal A) of the signal processing apparatus and the first component (i.e. component 210, 310 or 410). These additional components may also be coupled between the output terminal (i.e. terminal B) of the signal processing apparatus and the third component (i.e. component 230, 330 or 430). Since these additional circuit components do not affect the above-mentioned operations and functions of the inverting circuit, the filtering circuit, and the selecting circuit, these additional circuit components also fall within the scope of the present invention.

Figure 5:
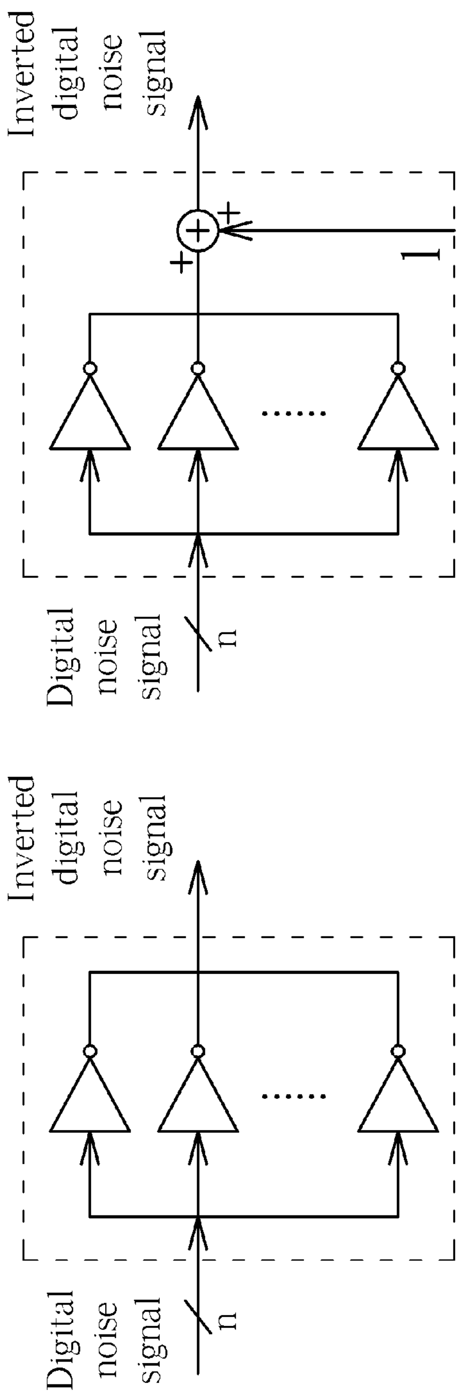
FIG. 5 illustrates a block diagram of an inverting circuit of the signal processing apparatus according to one exemplary embodiment of the present invention.

The inverting circuit of the inventive signal processing apparatus has a variety of possible implementations. For example, if a first signal received by the inverting circuit is a digital signal having at least one bit (e.g. n bits), the inverting circuit may comprises at least one NOT gate for inverting the at least one bit of the first signal to generate the inverted first signal. If the first signal carries information in the form of 2'complement (for example, if the first signal is a pulse coded modulation (PCM) signal), an adder will be used to add a binary “1” to the output of the NOT gate since the inverse of 2'complement needs a NOT operation and an addition of “1”. A corresponding illustrative diagram is shown in FIG. 5. Additionally, the inverting circuit could be implemented with an all-pass filter. If the noise signal is a periodical signal, the inverting circuit can be implemented with a delay circuit that generates a delay of certain amounts (e.g. half a period of the input signal), which results in a phase difference of 180 degrees between the input signal and the output signal, thereby obtaining the effect of anti-phase. It should be noted that the inverting circuit of the present invention can be implemented by any types of circuits having an inverting effect.

In other exemplary embodiments, in order to improve user comfort while listening to audio materials via the signal processing apparatus of the present invention, the present invention further introduces an evaluation mechanism, which evaluates energy of the noise signal to avoid the condition that the noise cancellation signal exists alone. In such a condition, the negative pressure caused by the noise cancellation signal will make users uncomfortable. The principle of the evaluation mechanism is to avoid the noise cancellation signal existing alone or being more severe. When the user turns on an anti-noise loudspeaker device provided with the inventive signal processing, the acoustic-to-electric transducer of the anti-noise loudspeaker generates a noise signal even if there is a weak noise in the environment. Normally, the user is not very sensitive to the noise at a very low level; however, if a weak noise signal is inverted and then generated by the loudspeaker device, a negative pressure will be generated, which is sensitive to users (if the loudspeaker device does not simultaneously produce normal audio signals, the negative pressure is more sensitive). Under such a condition, the evaluation mechanism will not allow the noise cancellation signal to be outputted to the back-stage circuit, or will not allow the signal processing apparatus to receive the noise signal, thereby avoiding the noise cancellation signal being played by the loudspeaker device. Further details are described in a fourth exemplary embodiment and a fifth exemplary embodiment.

Figure 6:
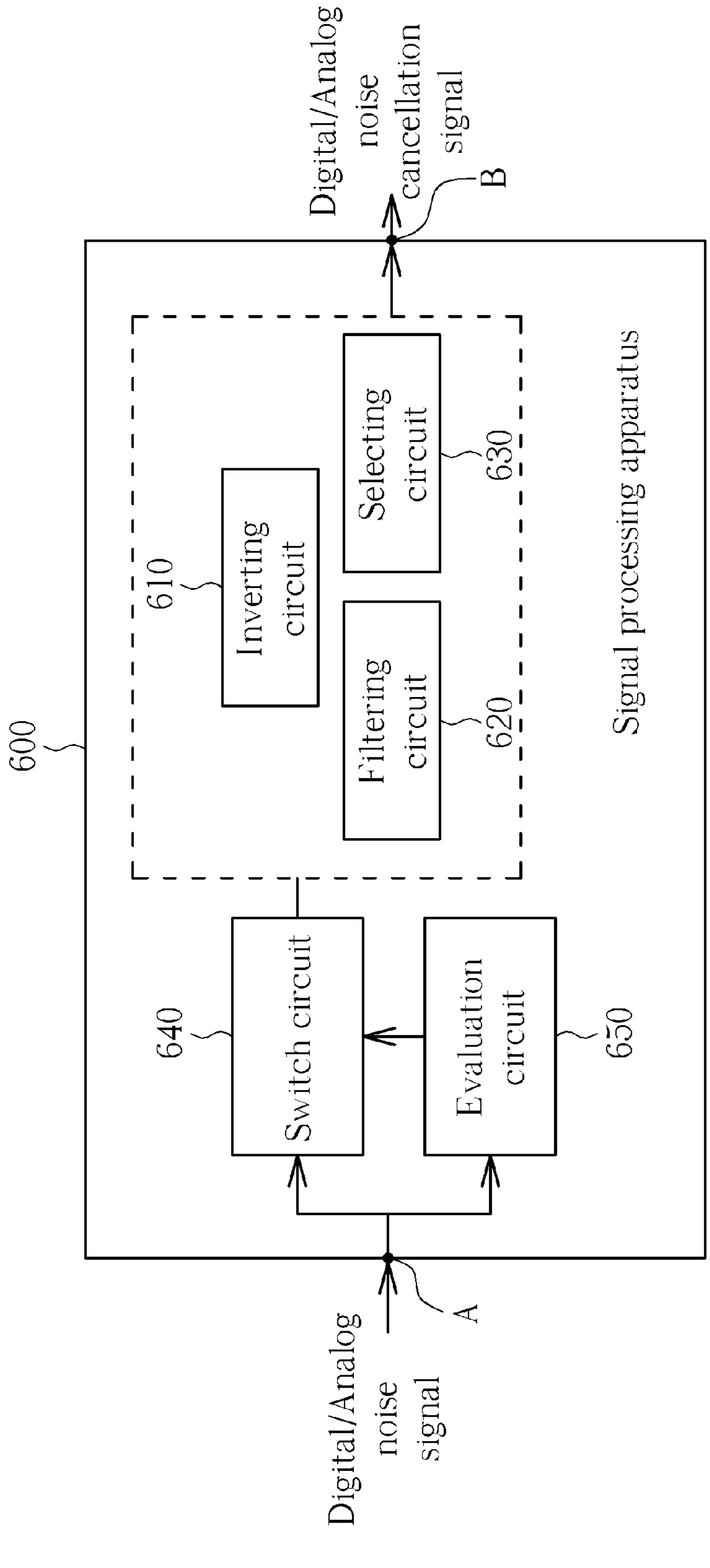
FIG. 6 illustrates a block diagram of a signal processing apparatus according to a fourth exemplary embodiment of the present invention.

FIG. 6 illustrates a signal processing apparatus according to the fourth exemplary embodiment of the present invention. The signal processing apparatus 600 comprises an inverting circuit 610, a filtering circuit 620 and a selecting circuit 630. Circuit connections in the signal processing apparatus 600 may be identical to one of the first, second and third embodiments. The signal processing apparatus 600 further comprises a switch circuit 640 and an evaluation circuit 650. The switch circuit 640 is disposed at the input terminal of the signal processing apparatus 600, and employed for controlling receiving of the noise signal to further determine whether or not to generate the noise cancellation signal. The evaluation circuit 650 is employed for evaluating an energy value corresponding to the noise signal (which may be a digitalized noise signal or an analog noise signal), and controlling the switch circuit 640 according to the energy value. When the energy value is not greater than a predetermined value (meaning the noise is too weak for a user to be aware of), the evaluation circuit 650 controls the switch circuit 640 to prevent the noise signal from being received by the signal processing apparatus 600 (which further leads to the result that the noise cancellation signal is not generated). When the value of the energy is greater than the predetermined value (meaning the noise is obvious to a user, and the noise cancellation is therefore necessary), the evaluation circuit 650 controls the switch circuit 640, allowing the noise signal to be received by the signal processing apparatus 600 (the signal processing apparatus 600 accordingly generates the noise cancellation signal). Hence, under some specific conditions, the noise cancellation signal will be not generated, thereby improving the user's comfort.

Figure 7:
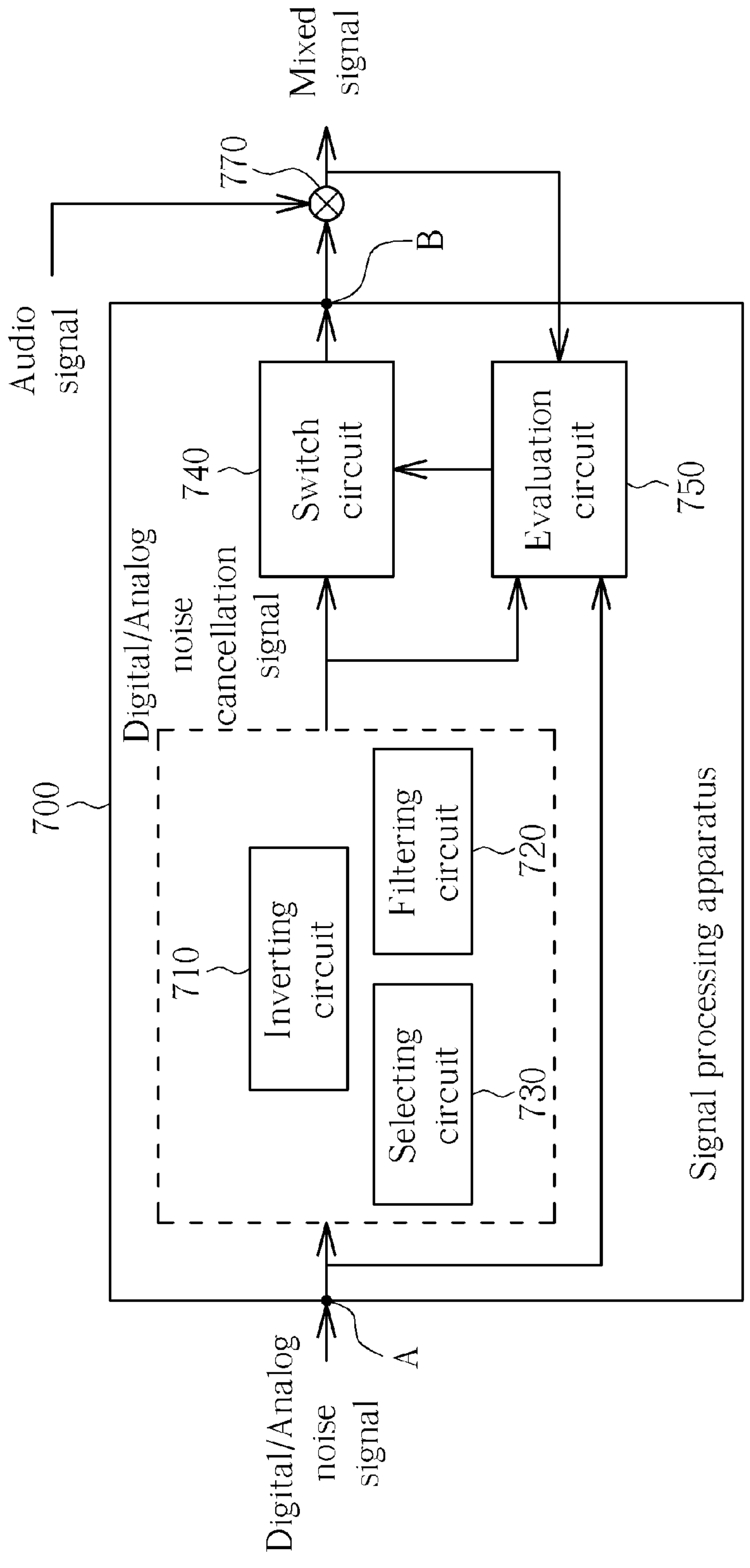
FIG. 7 illustrates a block diagram of a signal processing apparatus according to a fifth exemplary embodiment of the present invention.

FIG. 7 illustrates a signal processing apparatus according to a fifth exemplary embodiment of the present invention. The signal processing apparatus 700 comprises an inverting circuit 710, a filtering circuit 720 and a selecting circuit 730.

Circuit connections of the signal processing apparatus 700 may be identical to one of the first, second and third embodiments. The signal processing apparatus 700 further comprises a switch circuit 740 and an evaluation circuit 750. The switch circuit 750 is disposed at an output portion of the signal processing apparatus 700, and employed for controlling the outputting of the noise cancellation signal. The evaluation circuit 750 is employed for evaluating an energy value corresponding to an input signal (which may be an analog noise signal or a digitalized noise signal), and controlling the switch circuit 740 according to the energy value. The output signal may be generated depending on the noise signal, the noise cancellation signal, or even a mixed signal generated by mixing an audio signal with the noise cancellation signal (with the mixer 770). When the value of the energy is not greater than a predetermined value, the evaluation circuit 750 will control the switch circuit 740 to prevent the noise cancellation signal from being outputted by the signal processing apparatus 700. When the energy value is greater than the predetermined value, the evaluation circuit 750 controls the switch circuit 740, allowing the noise cancellation signal to be outputted by the signal processing apparatus 700. In addition, the evaluation circuit 750 can refer to other signals to control the switch circuit 740 to provide a more thorough and complete evaluation. Briefly, the signal that is inputted to the evaluation circuit 750 as a reference for determining how to control the switch circuit 740 may be the noise signal, the filtered noise signal, the output signal of the signal processing apparatus or a mixed signal of an audio signal and the output signal of the signal processing apparatus.

Figure 8:
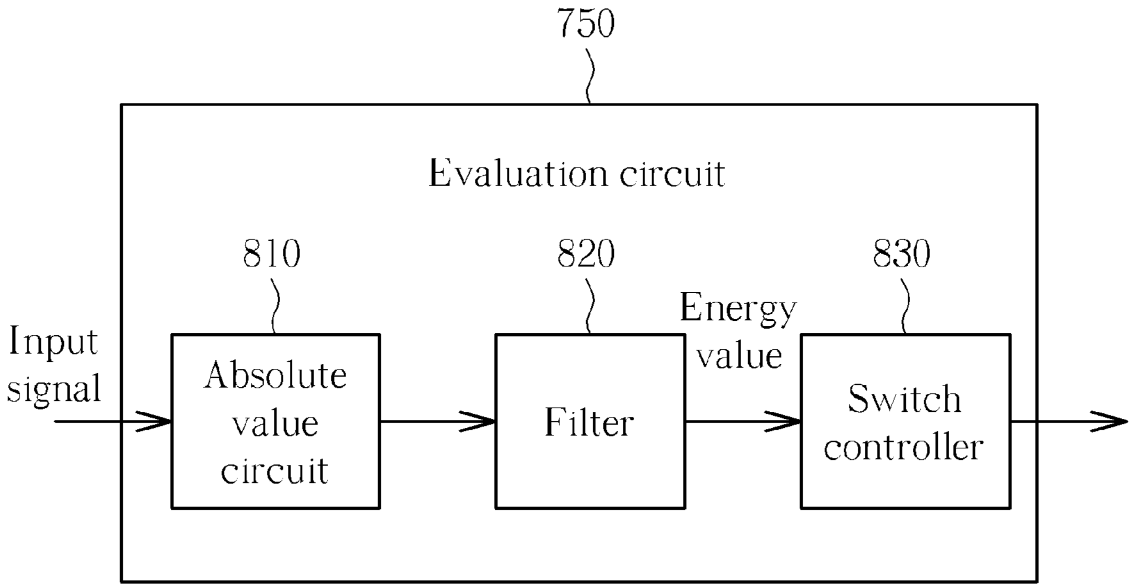
FIG. 8 illustrates a block diagram of an evaluation circuit of the signal processing apparatus according to one exemplary embodiment of the present invention.

The evaluation circuit 650 and 750 has a variety of possible implementations. Please refer to FIG. 8, which illustrates one possible implementation of the evaluation circuit. As shown in FIG. 8, the evaluation circuit 800 comprises an absolute value circuit 810, a filter 820 and a switch controller 830. The absolute value circuit 810 is employed for receiving and processing the noise signal (or the noise cancellation signal or the mixed signal), the filter 820 is employed for generating the energy value corresponding to the noise signal (or the noise cancellation signal or the mixed signal) according to the output of the absolute value circuit 810. The switch controller 830 is employed for generating a switch control signal to the switch circuit 640 and 740 according to the energy value. Alternatively, the absolute value circuit 810 may be replaced with a peak detector to provide the same function.

As mentioned above, the evaluation circuits 650 and 750 may refer to the noise signal, the noise cancellation signal or the mixed signal to control the switch circuit 640 and 740, thereby changing the signal transmission path of the signal processing apparatus 600 and 700 and controlling whether or not to generate/output the noise cancellation signal. In various embodiments of the present invention, it is also possible to achieve a similar effect by directly turning on/turning off the signal processing apparatus 600 and 700. One possible implementation is to control the power supply of the signal processing apparatus 600 and 700. By providing the power to or removing the power from the signal processing apparatus 600 and 700, the noise cancellation signal can be generated or not. Additionally, in various embodiments of the present invention, it is also possible to control circuit components inside the signal processing apparatus 600 and 700 with an enablement signal. By starting or terminating operations of the signal processing apparatus 600 and 700, power consumption of the signal processing apparatus 600 and 700 can be reduced to achieve the effect of power saving. In various embodiments of the present invention, the switch circuits 640 and 740 may not directly change the generation of the noise cancellation signal, instead the switch circuits 640 and 740 could control a gain applying to the noise cancellation signal. Specifically, when anti-noise is desired by the user, a larger gain will apply to the noise cancellation signal; contrarily when anti-noise is unwanted, a smaller gain will apply to the noise cancellation signal.

Figure 9:
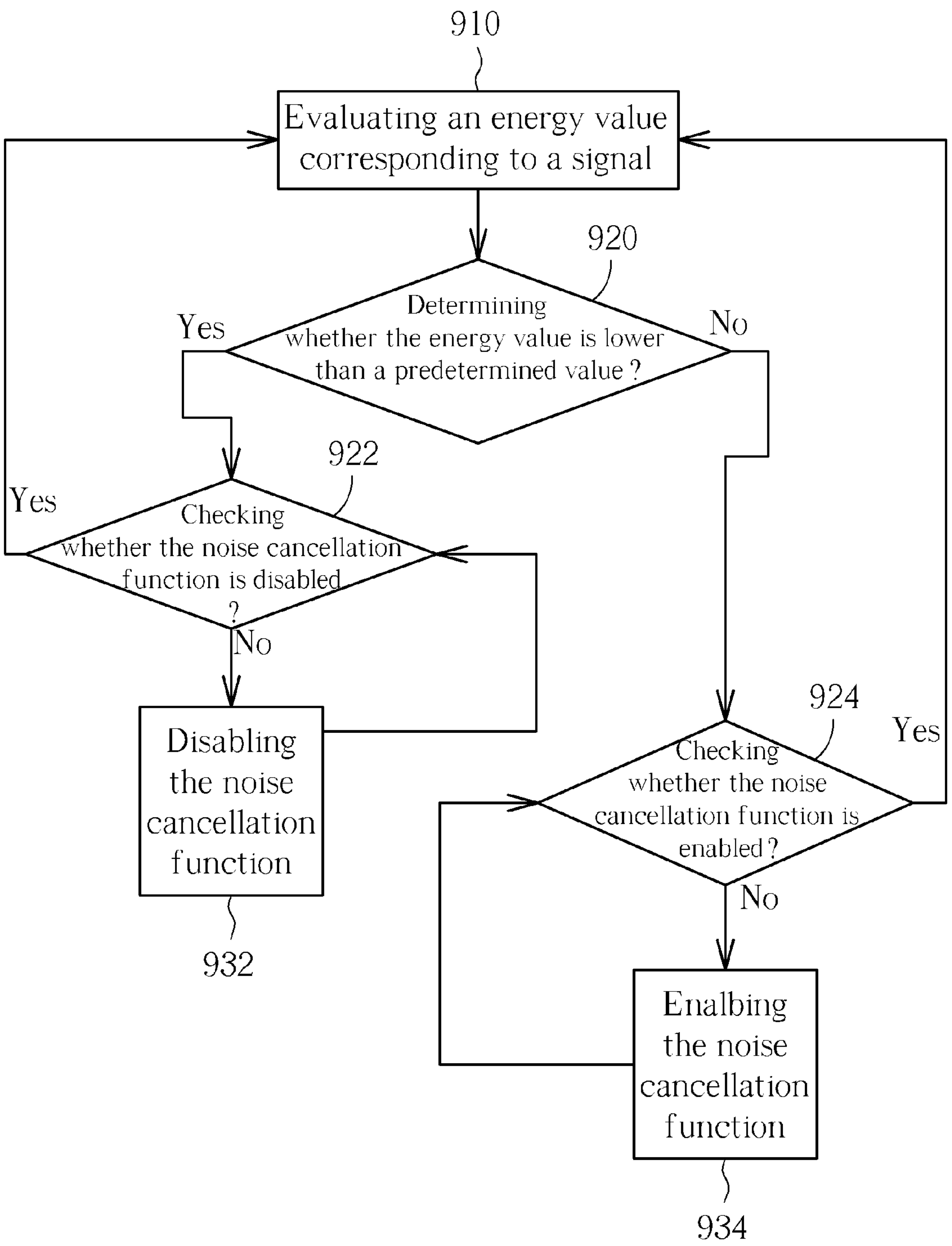
FIG. 9 illustrates a control flow of the signal processing apparatus according to one exemplary embodiment of the present invention.

Please refer to FIG. 9, which illustrates a control flow of a signal processing apparatus according to one exemplary embodiment of the present invention. As shown, in Step 910, the evaluation circuit inventive signal processing apparatus evaluates an energy value corresponding to a signal. The signal that is evaluated by the evaluation circuit may be a noise signal, a noise cancellation signal or a mixed signal. In Step 920, the evaluation circuit determines whether the energy value is lower than a predetermined value. Please note that the predetermined value changes depending on what signal is evaluated by the evaluation circuit. When the energy value is lower than the predetermined value, the flow goes to Step 922, in which it is checked whether the noise cancellation function is enabled, wherein enabling the noise cancellation function may refer to supplying power to the signal processing apparatus or turning on the switch circuit to change the signal transmission path of the signal processing apparatus to allow the signal processing apparatus to generate/output the noise cancellation signal. If the checking result of Step 922 is positive, the flow goes back to Step 910, in which the signal will be evaluated again. If, however, in Step 922 it is found that the noise cancellation function has not been disabled, the flow goes to Step 932, removing the power supplied to the signal processing apparatus, or controlling the switch circuit to change the signal transmission path which causes the signal processing apparatus not to generate/output the noise cancellation signal. If the result of Step 924 is positive, the flow goes to Step 910, wherein the energy of the signal is re-evaluated; otherwise, if the result of Step 924 is negative, indicating the noise cancellation function is not enabled, the flow goes to Step 934, in which the power will be supplied to the signal processing apparatus or the switch circuit will be controlled to change the signal transmission path to allow the signal processing apparatus to generate/output the noise cancellation signal.

In one exemplary embodiment, during the process of enabling/disabling the noise cancellation function, an exact timing to enable/disable the noise cancellation function according to the amplitude of an output signal of the signal processing apparatus (e.g. signal processing apparatus) is further determined in order to avoid a popping sound occurring at the moment of enabling or disabling. Only when the amplitude of the output signal is low enough will the noise cancellation function be immediately enabled/disabled (e.g. by changing the power supply or changing the signal transmission path) to determine whether to generate the output signal or not. If the amplitude of the output signal is not low enough, the present invention will not immediately enable/disable the noise cancellation function; instead, the present invention will wait until the amplitude of the output signal decreases to a low level, thereby avoiding the popping sound.

Figure 10:
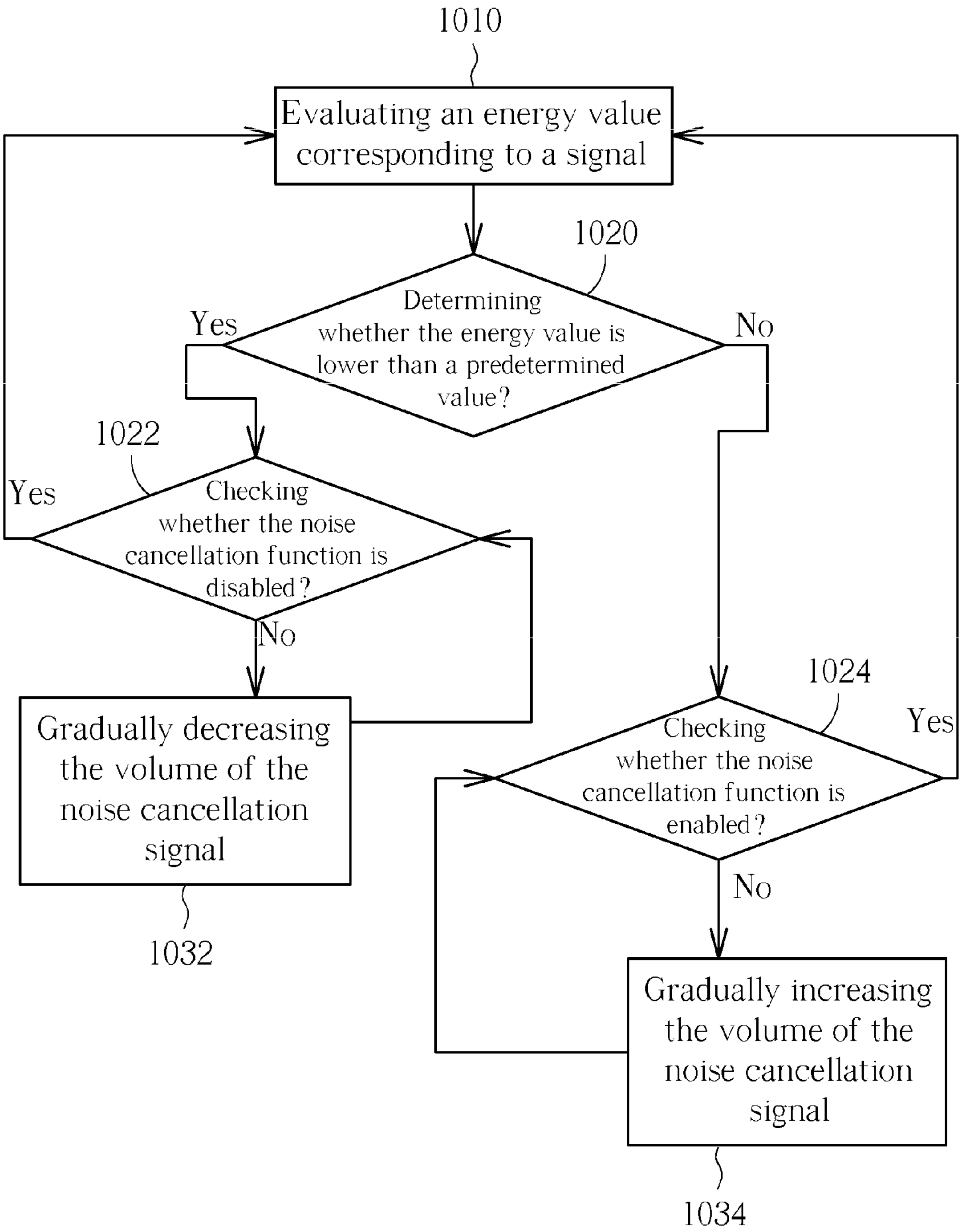
FIG. 10 illustrates a control flow of the signal processing apparatus according to another exemplary embodiment of the present invention.

Please refer to FIG. 10, which illustrates a control flow of the inventive signal processing apparatus according to another exemplary embodiment of the present invention. The difference between this embodiment and the embodiment disclosed in FIG. 9 is that, unlike in Step 932, Step 1032 in this embodiment will not directly disable the noise cancellation function, but will instead gradually decrease the volume of the noise cancellation signal, achieving a "fade out" effect. Similarly, in Step 1034, the inventive signal processing apparatus gradually increases the volume of the noise cancellation signal, achieving a "fade in" effect. By doing so, the use can obtain an enhanced listening experience.

Reference in the specification to "one embodiment" or "an embodiment" means that a particular feature, structure, or characteristic described in connection with the embodiment is included in at least an implementation. The appearances of the phrase "in one embodiment" in various places in the specification are not necessarily all referring to the same embodiment. Furthermore, although embodiments have been described in language specific to structural features and/or methodological acts, it is to be understood that claimed subject matter may not be limited to the specific features or acts described. Rather, the specific features and acts are disclosed as sample forms of implementing the claimed subject matter.

In summary, the signal processing apparatus of the present invention provides a variety of possible implementations to achieve noise cancellation and noise restraining. As a result, an unexpected constructive interference with the noise due to improper circuit design can be avoided.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A signal processing apparatus, for receiving a noise signal to generate a noise cancellation signal, comprising:
- an inverting circuit, for inverting a first signal to generate an inverted first signal;
- a selecting circuit, coupled to the inverting circuit, for selecting one of the first signal and the inverted first signal as an output signal;
- a switch circuit, coupled to the inverting circuit and the selecting circuit, for controlling an operation of the signal processing apparatus; and
- an evaluation circuit, coupled to the switch circuit, for evaluating an energy value corresponding to the first signal and controlling the switch circuit according to the energy value.

2. The signal processing apparatus of claim 1, further comprising:
- a filtering circuit, coupled to the selecting circuit, for filtering the output signal to generate the noise cancellation signal, wherein the first signal is the noise signal.

3. The signal processing apparatus of claim 1, further comprising:
- a filtering circuit, coupled to the inverting circuit, for filtering the noise signal to generate the first signal.

4. The signal processing apparatus of claim 1, wherein the first signal is a digital signal having at least one bit; the inverting circuit comprises at least one NOT gate, and the inverting circuit is utilized for inverting the at least one bit of the first signal to generate the inverted first signal according to a result of inverting.

5. The signal processing apparatus of claim 1, wherein the first signal is a digital signal having at least one bit; the inverting circuit comprises at least one NOT gate, and the inverting circuit is utilized for inverting the at least one bit of the first signal to generate a result, and the inverting circuit further comprises:
- an adder, for adding a binary one to the result to generate the inverted first signal.

6. The signal processing apparatus of claim 1, wherein the inverting circuit comprises an all-pass filter and the inverting circuit generates the inverted first signal by the all-pass filter filtering the first signal.

7. The signal processing apparatus of claim 1, wherein the inverting circuit comprises a delay circuit, the inverting circuit generates the inverted first signal by the delay circuit delaying the first signal; and the first signal is a periodical signal.

8. The signal processing apparatus of claim 1, wherein when the energy value is not greater than a predetermined value, the evaluation circuit controls the switch circuit to prevent the signal processing apparatus from outputting the output signal, and when the energy value is greater than the predetermined value, the evaluation circuit controls the switch circuit to cause the signal processing apparatus to generate the output signal.

9. The signal processing apparatus of claim 1, wherein the evaluation circuit comprises an absolute value circuit, a filter and a switch controller; the absolute value circuit receives and processes the first signal, the filter outputs the value of the energy corresponding to the first signal according to an output from the absolute value circuit, and the switch controller generates a switch control signal to the switch circuit according to the energy value.

10. The signal processing apparatus of claim 1, wherein the evaluation circuit comprises a peak detector, a filter and a switch controller, the peak detector receives and processes the first signal, the filter outputs the energy value according to an output from the peak detector, and the switch controller generates a switch control signal to the switch circuit according to the energy value.

11. The signal processing apparatus of claim 1, wherein when the energy value is not greater than a predetermined value, the evaluation circuit turns off the signal processing apparatus, preventing the signal processing apparatus from generating the output signal, and when the energy value is greater than the predetermined value, the evaluation circuit turns on the signal processing apparatus, causing the signal processing apparatus to generate the output signal.

12. The signal processing apparatus of claim 1, wherein if the amplitude is smaller than the reference amplitude, the evaluation circuit controls the signal processing apparatus according to the energy value.

* * * * *